United States Patent [19]

Tidwell et al.

[11] Patent Number: 4,940,723

[45] Date of Patent: Jul. 10, 1990

[54] USE OF BIS-(5-AMIDINO-2-BENZIMIDAZOLYL) METHANE (BABIM) TO TREAT ARTHRITIS

[75] Inventors: Richard R. Tidwell; Joachim D. Geratz; John H. Schwab; Katherine B. Pryzwansky; Sonia K. Anderle, all of Chapel Hill, N.C.

[73] Assignee: University of North Carolina, Chapel Hill, Chapel Hill, N.C.

[21] Appl. No.: 260,056

[22] Filed: Oct. 20, 1988

[51] Int. Cl.⁵ ............................................ A61K 31/415
[52] U.S. Cl. ..................................... 514/396; 514/401
[58] Field of Search ................................ 514/401, 396

[56] References Cited

PUBLICATIONS

Dieter et al. "Suppression of Streptococcal Cell Wall-Induced Arthritis by a Potent Protease Inhibitor, Bis-(5-Amidino-2-benzimidazolyl)methane", Arthritis and Rheumatism, vol. 31, No. 9 (Sep. 1988).

Jennette et al. "Amelioration of Immune Complex-Mediated Glomerulonephritis by Synthetic Protease Inhibitors", American Journal of Pathology, vol. 127, No. 3, Jun., 1987.

Gallin et al. Inflammation, Basic Principles and Clinical Correlates, Raven Press, 1988, Chapter 50 by P. E. Lipskey, "Gold, Penicillamine, and Antimalarials", pp. 897-910.

Stecher et al. "Disease-Modifying Anti-Rheumatic Drugs", Medicincal Research Reviews, vol. 5, No. 2, pp. 371-390 (1985).

Chem. Abst. vol. 108 (1988)-106095y.

Chem. Abst; vol. 109 (1988)-183228s.

*Primary Examiner*—Stanley J. Friedman
*Attorney, Agent, or Firm*—Cushman, Darby & Cushman

[57] ABSTRACT

A method of treating arthritis, and/or bone marrow hyperplasia, osteitis and synovitis, and/or granulomatosis including of the liver and spleen, which comprises administering to a patient an effective amount of BABIM and a pharmaceutically acceptable carrier.

8 Claims, 5 Drawing Sheets

USE OF BIS-(5-AMIDINO-2-BENZIMIDAZOLYL) METHANE (BABIM) TO TREAT ARTHRITIS

BACKGROUND OF THE INVENTION

The present application relates to a method for treating arthritis and more particularly relates to treating arthritis by use of bis-(5-amidino-2-benzimidazoly) methane (BABIM). The use of BABIM represents a novel approach to the suppression of arthritis and coincidental conditions including liver and spleen granulomata.

Arthritis is a polyarticular inflammatory process characterized by episodic remissions and exacerbations and by progressive loss of joint function. It has a prevalence rate of about 0.5% in women and 0.1% in men begins commonly in the prime of life and exacts a high toll in morbidity and personal suffering. Treatment has been with a variety of nonsteroidal antiinflammatory agents (NSAIA), usually in combination with a modifying drug. NSAIA can mitigate pain and inflammation by interference with prostaglandin synthesis, but are unable to arrest the basic destructive properties of the disease. Response-modifying compounds, such as gold salts or methotrexate can retard or block the pathogenic events, yet are restricted in their long-term usefulness by significant adverse side effects.

BRIEF SUMMARY OF THE INVENTION

A novel approach to the treatment of arthritis has been newly found employing the realization that proteolytic enzymes are prominently involved in many phases of inflammation and that inhibitors may succeed in interrupting the undue enzymatic activity. Many of the suspect protease, such as Factor XIIa, thrombin, plasmin and kallikrein, are trypsin-like in nature. They have in common the ability to hydrolyze arginyl and lysyl bonds and also share the susceptibility to inhibition by synthetic amidino compounds. Amidines have already proven themselves as potent drugs in a variety of pathologic states. They can serve as strong anticoagulants, block protease-dependent replication of respiratory syncytial virus and rotavirus, retard tumor invasion and metastasis, and eliminate the characteristic glomerular necrosis seen in immune complex-mediated glomerulonephritis.

In one embodiment of the present invention, BABIM a potent inhibitor of trypsin, plasmin and urokinase, is used to treat and suppress arthritis. The disease model chosen was that of type A streptococcal peptidoglycan polysaccharide (PG-APS)-elicited erosive inflammation which is representative of and duplicates many of the features of immune-based arthritis in humans. This is one of the best models for human arthritis.

Additional embodiments of the present invention include treatment with BABIM to reduce granulomatous lesions of spleen and liver.

BRIEF DESCRIPTION OF THE DRAWINGS

Further, objects and advantages of the present invention will be better understood by carefully reading the following detailed description of the presently preferred exemplary embodiments of this invention in conjunction with the accompanying drawings, of which.

DETAILED DESCRIPTION OF THE INVENTION

Since its establishment as a research method, PG-APS-induced joint disease has been studied extensively to clarify various aspects of the arthritic process. It was found that the tissue reactions are tied to the presence of PG-APS fragments in the areas involved and that the initial acute inflammatory response and the recurrences happen in a stereotyped predictable manner. Complement activation has been identified as a factor in the early, but not in the later events while the converse has been found true for T cell participation. Furthermore, the genetic background of the experimental animals is of prime importance for the reactivity to cell wall polymers. For example, Sprague-Dawley as well as Lewis rats, develop crippling arthritis in response to systemic application of crude whole streptococcal cell wall sonicates, yet Buffalo rats are resistant to this stimulus. Lewis rats again are different from other strains in their tendency to produce granulomata around cell wall deposits in the liver and in the extent of bone remodeling and joint erosion. Sprague-Dawley rats, though showing similar intrahepatic accumulations of potentially antigenic material seem unable to mount a reaction against it. The established granulomata in the Lewis rats have been described and shown in illustrations as being made up of macrophages and lymphocytes surrounded by a peripheral zone of fibroblasts. The Lewis rat is the best for representing arthritis in humans.

Experiments which further disclose the present invention showed three additional histopathologic findings relating animals having PG-APS injection. There were numerous granulomata not only in the liver, but also in the spleen. There was prominent central necrosis in those lesions. And, there was striking hematopoietic proliferation in the distal portions of the extremities and in the spleen. The intrahepatic and intrasplenic granulomata were identical in their cellular makeup, but their stellate, or branching pattern in the spleen was quite different from their round shape in the liver. Necrosis was a late occurrence in the granulomata and was a consequence of a heavy influx of polymorphonuclear leukocytes and their resulting breakdown. The histological pattern is reminiscent of what is observed in lymph nodes of patients with cat scratch disease, tularemia or lymphogranuloma venereum. The morphologic similarity of all those conditions may be an expression of the same pathogenetic mechanism set in motion by disparate agents.

Discovery of the hematopoietic hyperplasia in cell wall-treated animals was an unexpected finding. For accurate judgement of the phenomenon, the skeleton and the spleen were examined in non-arthritic Lewis rats of the same body weight as the PG-APS treated experimental animals. It was found that at this stage in their life the animals had active trilineage hematopoiesis with 95–100% cellularity in the sternum, the vertebrae, the humeri, and the femora. The radii, ulnae, tibiae, and fibulae were similarly packed with cells down to the distal metaphyseal areas where fat cells became more abundant. Adipose tissue was present nearly exclusively in the marrow spaces of the foot bones. Thus, the presence of hematopoiesis in those latter sites in cell wall-treated rats is distinctly abnormal. Also the spleens in the control group without the cell-wall injection showed only a few foci of blood cell precursors and rare megakaryocytes.

Pathogenetically, neutrophilic infiltration into streptococcal cell wall-induced granulomata was most likely the result of interleukin-1 production by the phagocytic component of the lesions. Interleukin-1 is an effective chemotactic agent for neutrophils and is known to be present in abundance in the granulomata during the early weeks of their evolution. Hematopoietic hyperplasia was probably also under control by cytokine(s), such as interleukin-3.

The striking antiarthritic effect of BABIM supports the initial premise that trypsin-like proteases play a significant role in the inflammatory process and that inhibition of those enzymes may abort the pathogenetic events. The recurrence of the disease was blocked as completely as the primary response. This may mean either that identical reactions were interfered with on both occasions or that BABIM inhibits more than one step in the inflammatory cascade. Interruption of complement activation along the classical pathway has been held responsible for the beneficial influence of FUT-175, another synthetic trypsin inhibitor, on adjuvant arthritis in Sprague-Dawley rats. Such explanation is unlikely in this case because BABIM is only weakly inhibitory in assays of Clr and Cls and in hemolytic complement tests.

The pristine appearance of joints and bone marrow spaces in cell wall-injected and BABIM-treated Lewis rats suggests that the inhibitor suppresses very early protease-dependent activities, such as the chemoattractant and kinin generating properties of kallikrein. However, there are numerous other early and late opportunities for antiproteolytic intervention. Though most of the evidence comes from data on mouse or human cells, similar processes can probably be blocked in rat cells. At points of neutrophils, there are the aggregation by kallikrein, thrombin and Factor XIIa, the release of granules by kallikrein and Factor XIIa, the cytolysis of target cells, the activation of released procollagenase by plasmin and kallikrein, and the activity of released plasminogen activator. With respect to macrophages, one could expect elimination of plasmin-stimulated interleukin-1 release and of the activation and action of procollagenase and plasminogen activator, respectively. As to lymphocytes, there could be interruption of protease-dependent transmembrane signalling in cytotoxic T cells, and of B cell mitogenic events as set in motion by either B cell-associated or cytolytic T cell-derived trypsin-like protease.

When comparing the ability of BABIM to suppress the various expressions of PG-APS-elicited disease, it is obvious that the arthritis component was more effectively dealt with than the hepatic and splenic granulomatous response. This might have been the larger concentrations of cell wall deposits in liver and spleen than in joint tissues. The anatomical peculiarities of the different sites, however, might also have been of importance.

The laboratory experiments have shown the great antiarthritic effectiveness of BABIM using laboratory test animals i.e. the well known Lewis rat. Skilled persons in the present art will recognize and accept these experiments as appropriately correlated with human utility for antiarthritic effectiveness and effectiveness for suppressing granulomata in liver and spleen.

EXAMPLES

The present invention will now be further shown by, but is by no means limited to, the following examples.

MATERIALS AND METHODS

Preparation of streptococcal cell wall fragments

Peptidoglycan-polysaccharide cell wall components were obtained from group A beta-hemolytic streptococci (type 3, strain D-58). The bacteria were grown to the early stationary phase in a 15-liter fermentor under aerobic conditions. After being harvested by continuous-flow centrifugation, they were homogenized and crudely fractionated by further centrifugation. The supernatant cell wall fragments underwent repeated extractions and washings and were finally dialyzed and lyophilized. Before administration to the Lewis rats, the material was resuspended in phosphate-buffered saline (PBS), sonicated, and centrifuged at 10,000 xg for 30 min. The supernatant fraction 10S represented the cell wall sample used in the current experiments. Details of the procedures are well known.

Quantification of PG-APS deposits in liver tissue

Measurements were based on a solid-phase enzyme-linked immunosorbent assay (ELISA) as known in the art. Briefly, microtiter plates were charged with group A cell wall antibodies and non-specific binding sites were blocked with human albumin. The coated walls were interacted with the tissue samples, and retention of PG-APS was determined from phosphate hydrolysis following sequential addition of affinity-purified biotinylated cell wall antibodies, avidin-alkaline phosphatase complexes and enzyme substrate. Standard curves were prepared with various amounts of the 10S PG-APS material and were used to correlate enzyme activity with levels of tissue deposits.

Trypsin inhibitor BABIM

BABIM was synthesized according to established procedures. Purity of the compound was ascertained by infrared and nuclear magnetic resonance spectroscopy, thin-layer chromatography and elemental analysis. The compound was easily dissolved in isotonic saline. Solutions were prepared fresh on the day they were used.

Administration of BABIM

Inbred female Lewis rats were purchased from Charles River Laboratories, Inc. Their mean body weight at the start of the study was 145 g. Arthritis was induced by a single intraperitoneal injection of the 10S fraction of purified cell wall material in PBS. The volume was 0.5 ml, and the dose of PG-APS was equivalent to 15 μg of rhamnose content per gram of body weight. For the administration of BABIM into the tail vein the animals were lightly anesthetized with ether. The inhibitor was contained in 0.1 ml of saline. Control animals were injected in the same way, but received saline only. All rats had free access to food and water. Nineteen days after the initiation of arthritis, they were killed with an overdose of ether.

Clinical scoring of the joint disease

Severity of the arthritis was judged daily for the first 11 days after PG-APS injection and every one to three days. Involvement of each extremity was quantified on a scale from 0-4, yielding a maximum combined score of 16. Grading was restricted to the wrist and ankle joints and all joints distal from there. The individual score was based on the number of joints involved, the degree of cutaneous erythema, the extent of the swelling of the skin and periarticular soft tissue, and the enlargement and deformities of the joints.

Histological methods

After the rats were killed, autopsies were performed. The liver, spleen, kidneys, adrenal glands, and the skinned distal hind legs were saved for further examination. The livers were weighed individually, and a sample of each was frozen and held for ELISA of PG-APS fragments. All other tissues were fixed in phosphate-buffered formalin solution. The bones were decalcified in formic acid-sodium citrate solution. Sections were stained with hematoxylin and eosin.

Histological grading of the severity of the arthritis

For this evaluation the hind legs were used because they were more severely involved than the front legs. Both hind legs were studied, but as the disease processes were always symmetrical only one leg was scored. Included in the histologic sections were the distal tibia with the ankle joint, the tarsal bones, and the metatarsals. These were ranked on a scale of 0-4, based on the extent of bone marrow hyperplasia, the density of neutrophilic infiltration in bone and soft tissues, the degree of destruction of trabecular and cortical bone, and the magnitude of the synovial and periosteal proliferative response.

Clinical antiinflammatory effects of BABIM

The basic design of the experiments was as follows. Arthritis was induced in two groups of rats by the intraperitoneal application of PG-APS fragments. One group of animals received repeated injections of BABIM dissolved in saline, while the other group received saline only. The inhibitor dose of 10 mg/kg body weight was selected because it has been found effective in preliminary studies. Those earlier investigations had also revealed a uniform response to the drug so that large numbers of animals were not needed to obtain unequivocal data.

Figure 1:
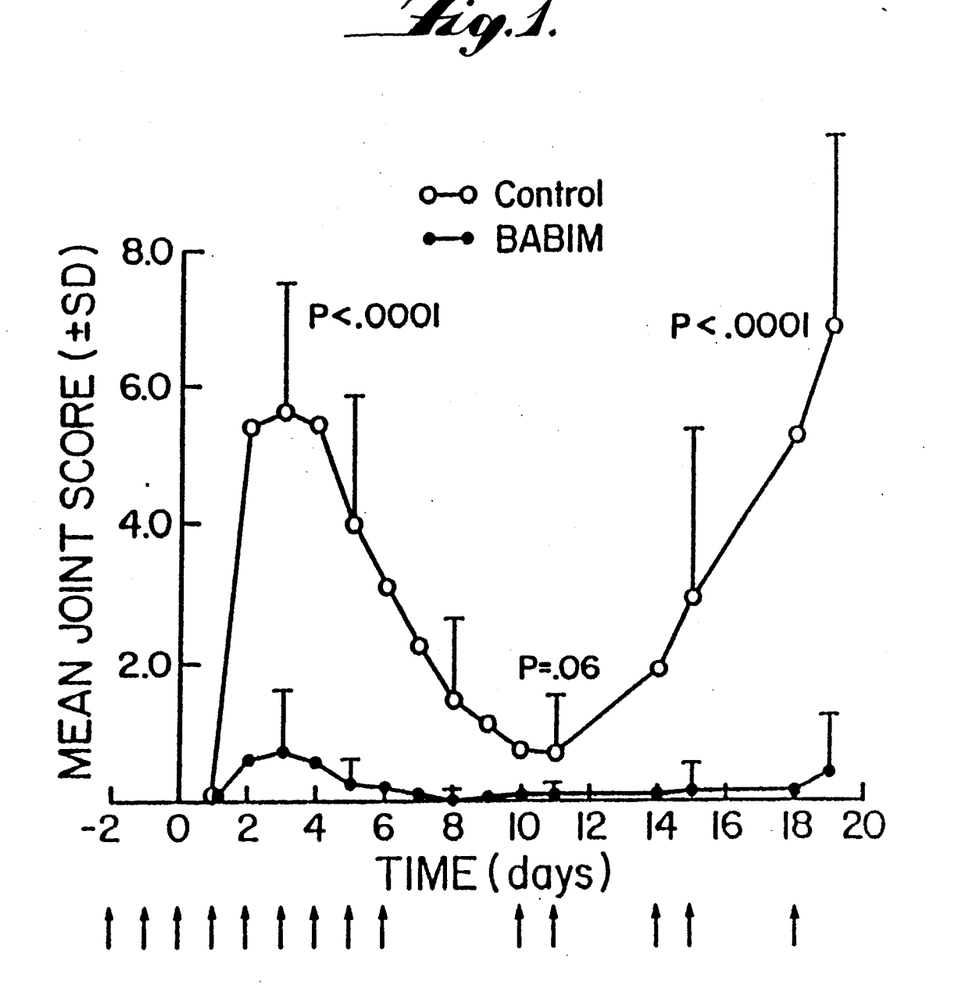
FIG. 1 shows clinical arthritis scores for vehicle-treated (n=8) and BABIM treated (n=7) Lewis rats, over a period of 19 days after initiation of the disease. Vehicle or BABIM was injected on the days indicated by arrows.

The dosing with inhibitor was begun two days before the induction of arthritis and was continued on a daily basis through day 6. From
then on injections were spaced 1-3 days apart. As shown in FIG. 1, BABIM suppressed the clinical signs of arthritis dramatically. It greatly reduced not only the initial inflammatory response, but also the recurrence that followed short-lived remission. From an examination of the individual arthritis scores that were used to calculate the mean values in FIG. 1 (data not shown), it was evident that all untreated animals had severe joint disease at the time of the first peak as well as at the time of recurrence. In contrast, 3 of the 7 treated rats were completely free of arthritis at the initial peak, and five of the seven were without symptoms during the recurrence. An additional clinical feature of the untreated animals, but not the treated animals, was a progressively increasing size of the liver, which became easily palpable below the costal margin. None of the recipients of BABIM showed any physical or behavioral abnormalities which might have been caused by the drug. Histological examination of the liver, kidney, adrenal glands, and spleen confirmed the absence of BABIM related toxicity.

Histological features of PG-APS-induced arthritis and their modification by BABIM Table 1 lists the clinical scores on the final day of the experiment together with the histological scores for the inhibitor-treated and the untreated animals. The data attest to the ability of the clinical grading system to predict the presence or absence of histological joint involvement. The data also confirm, at the microscopic level, the remarkable antiarthritic properties of BABIM.

Figure 2A:
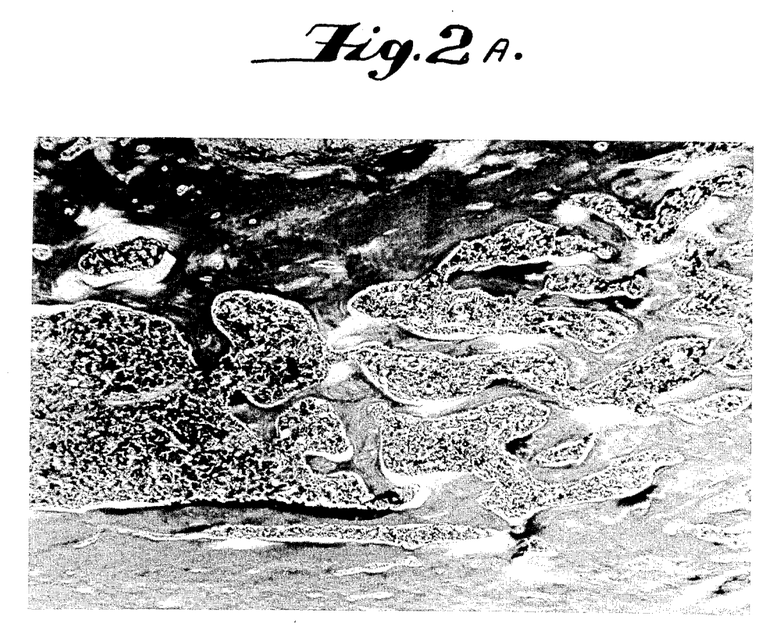
FIG. 2 shows bone marrow composition in the body of the calcaneus of 2 Lewis rats 19 days after initiation of arthritis. A Marrow spaces are tightly packed with hematopoietic elements in vehicle-treated rat. B, Predominantly fatty marrow in rat treated with BABIM. (Original magnification $\times 44$.)

The streptococcal cell wall-induced changes in the untreated control animals involved the bones as well as the joints of the foot and ankle. A distinctive and universal finding was the extensive replacement of the normally fatty bone marrow by closely packed hematopoietic cells (FIG. 2A).

TABLE 1

Severity of arthritis in vehicle-treated and bis(5-amidino-2-benzimidazolyl) methane (BABIM)-treated rats, as expressed by the clinical scores on the final day of the experiment and by histologic scores*

| Vehicle-treated rats | | | BAMIM-treated rats | | |
|---|---|---|---|---|---|
| Animal | Clinical score | Histologic score | Animal | Clinical score | Histologic score |
| 1 | 7.5 | 3 | 1 | 0 | 0 |
| 2 | 7.5 | 2.5 | 2 | 1 | 1.5 |
| 3 | 7 | 3 | 2 | 0 | 0 |
| 4 | 7.5 | 3.5 | 3 | 0 | 0 |
| 5 | 7 | 3 | 5 | 0 | 0 |
| 6 | 4 | 2.5 | 6 | 2 | 1 |

TABLE 1-continued

Severity of arthritis in vehicle-treated and bis(5-amidino-2-benzimidazolyl) methane (BABIM)-treated rats, as expressed by the clinical scores on the final day of the experiment and by histologic scores*

| Vehicle-treated rats | | | BAMIM-treated rats | | |
|---|---|---|---|---|---|
| Animal | Clinical score | Histologic score | Animal | Clinical score | Histologic score |
| 7 | 2 | 2 | 7 | 0 | 0 |
| 8 | 11.8 | 3 | | | |
| Mean ± SD | 6.79 ± 2.86 | 2.81 ± 0.46 | | 0.43 ± 0.79** | 0.36 ± 0.63** |

*Clinical involvement was scored on a scale of 0–4 (maximum combined score 16), and histologic findings were scored on a scale of 0–4 (see Materials and Methods for details).
**$P < 0.0001$ versus vehicle-treated animals.

Figure 3A:
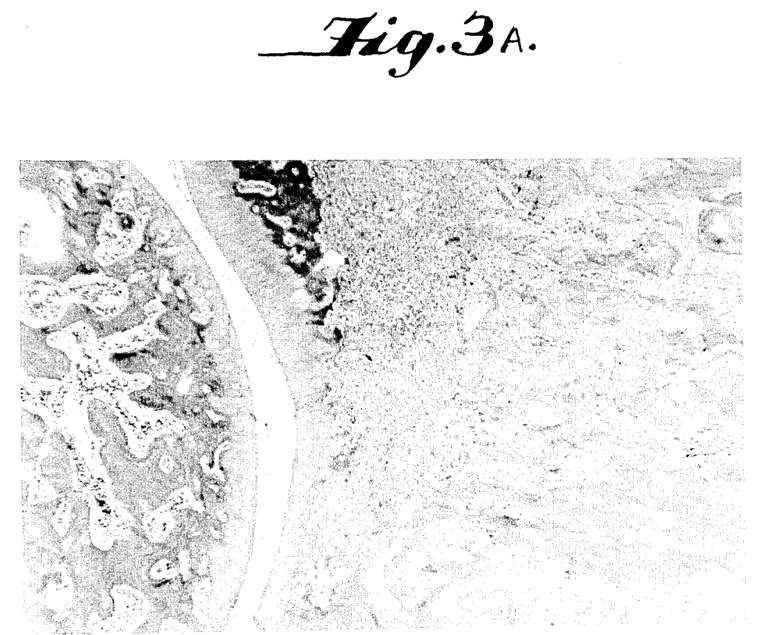
FIG. 3 shows ankle joints of 2 Lewis rats 19 days after initiation of arthritis. The tibia is on the right side of the joint space and the talus is on the left. A, Extensive destruction of the epiphysial plate and the epiphysial an metaphyseal bone trabeculae in the tibia of the vehicle-treated with BABIM (Original magnification $\times 44$)

There was proliferation of erythroid, myeloid and megakaryocytic elements. In more advanced lesions, the trilineage hyperplasia yielded to a predominance of mature neutrophils, which was accompanied by the appearance of multinucleated resorptive giant cells. This process took place in the short bones as well as the long bones, but was especially noticeable in the metaphyseal region of the distal tibia (FIG. 3A) and in the calcaneus. The infiltration led to destruction of bone trabeculae and the breakdown and removal of epiphyseal cartilage. Once the destruction was complete, the number of neutrophils declined leaving behind a loose tissue of fibroblasts and sinusoidal vessels. Attempts at repair, with accumulation of nests of osteoblasts and formation of new bone, were the final events in this evolutionary sequence.

Figure 4A:
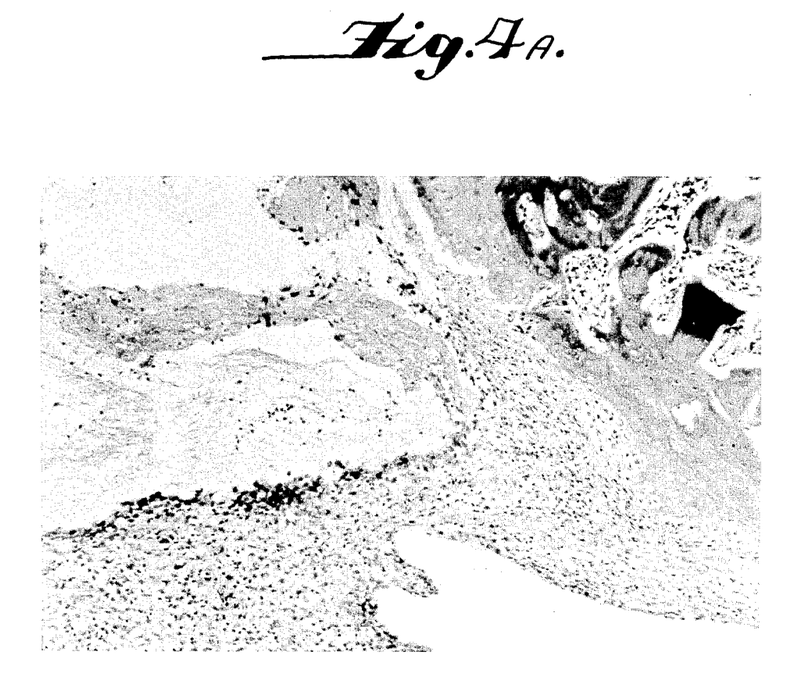
FIG. 4 shows synovial recess of ankle joints of 2 Lewis rats 19 days after initiation of arthritis. A, Acute synovitis with stromal edema and neutrophilic infiltration, an intraarticular inflammatory exudate, and early marginal erosion of the joint cartilage in the section from the vehicle-treated animal. B, In the animal treated with BABIM inflammation is absent. (Original Magnification $\times 107$)

Besides marrow hyperplasia and florid osteitis all untreated rats also showed acute synovitis (FIG. 4A) and focal periostitis. The synovial involvement consisted of lining cell hyperplasia, edema, neutrophilic infiltration, and, in the later stages, fibroblastic proliferation. A fibrinous exudate admixed with neutrophils was found in some of the synovial recesses. Lymphocytes were generally present only in small numbers. Destruction of marginal joint cartilage by early pannus formation was noted (FIG. 4A). The periosteum was hypercellular in many areas because of an increase in mesenchymal elements and the presence of scattered neutrophils. Subperiosteal bone erosion was encountered in some areas, but subperiosteal new bone formation was generally more striking.

Figure 2B:
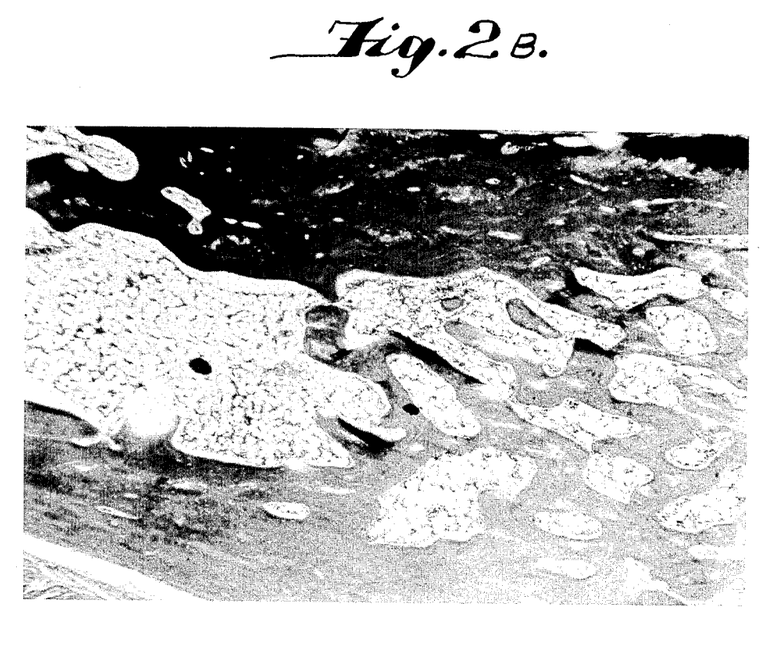
Figure 3B:
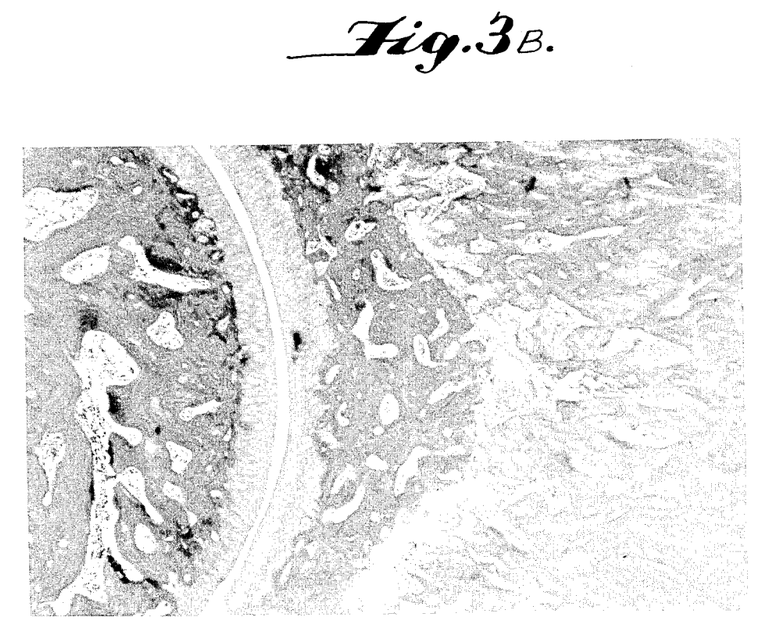
Figure 4B:
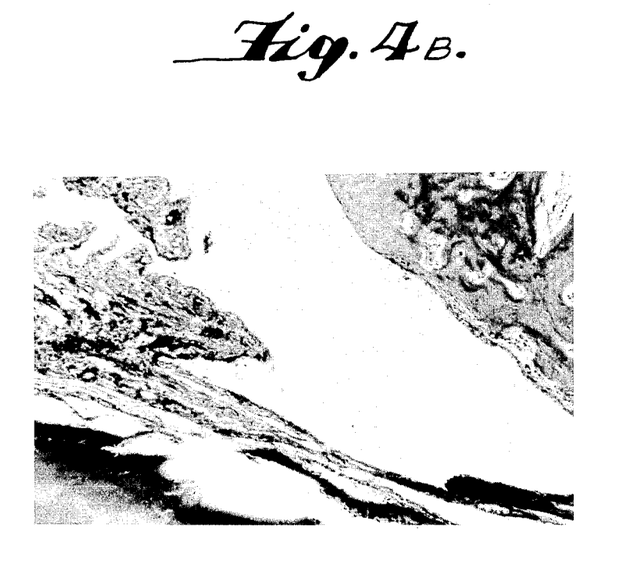

Hence, untreated rats showed a characteristic triad of hematopoietic marrow hyperplasia, destructive osteitis and acute synovitis. The same changes, although on a much smaller scale, were found in the two BABIM-treated animals which had developed joint disease. The other five BABIM-treated animals showed a complete absence of abnormalities (FIGS. 2B, 3B, and 4B) and had a histologic appearance similar to that of the rats that had never received injections of PG-APS fragments.

Figure 5A:
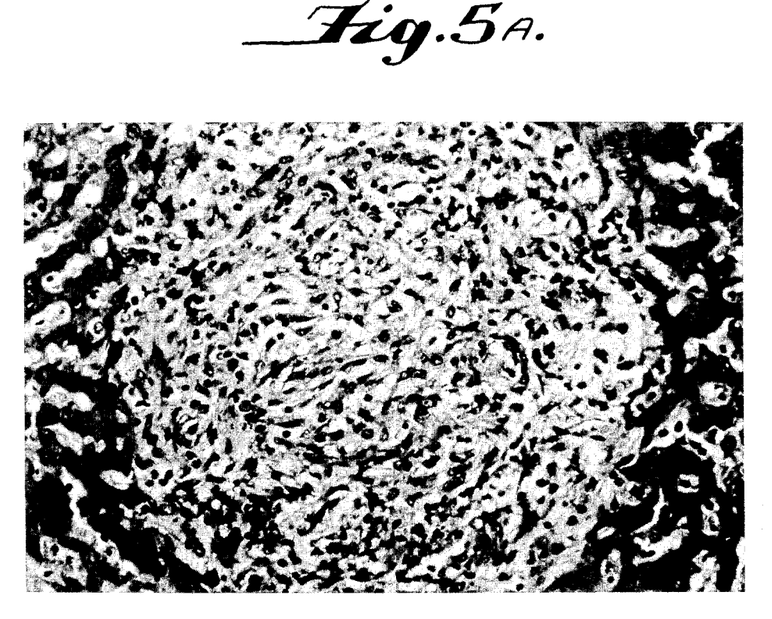
FIG. 5 shows hepatic, granulomata in 3 vehicle-treated Lewis rats 19 days after initiation of arthritis. A, Predominantly histiocytic granuloma without neutrophils. B, Early central immigration of neutrophils. C, Heavy central accumulation of neutrophils with associated necrosis. (Original magnification $\times 267$.).
Figure 5B:
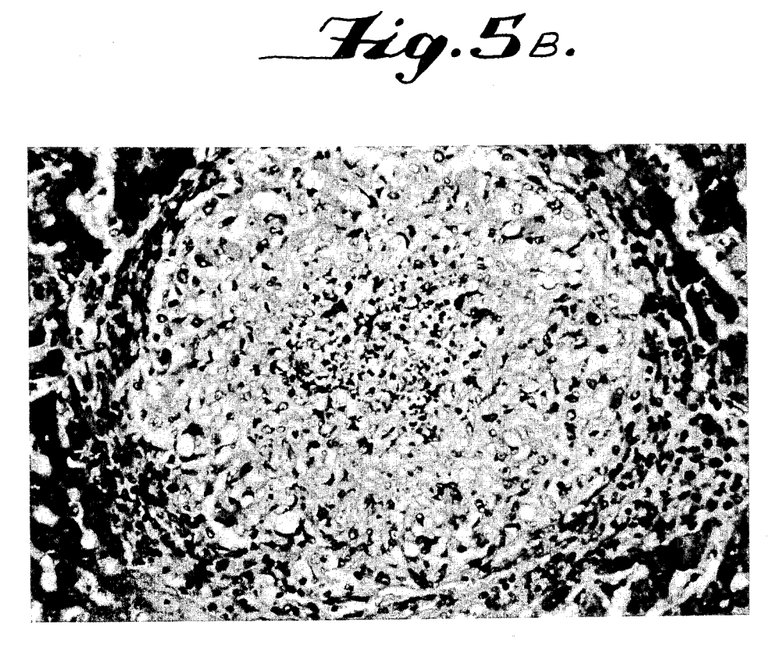
Figure 5C:
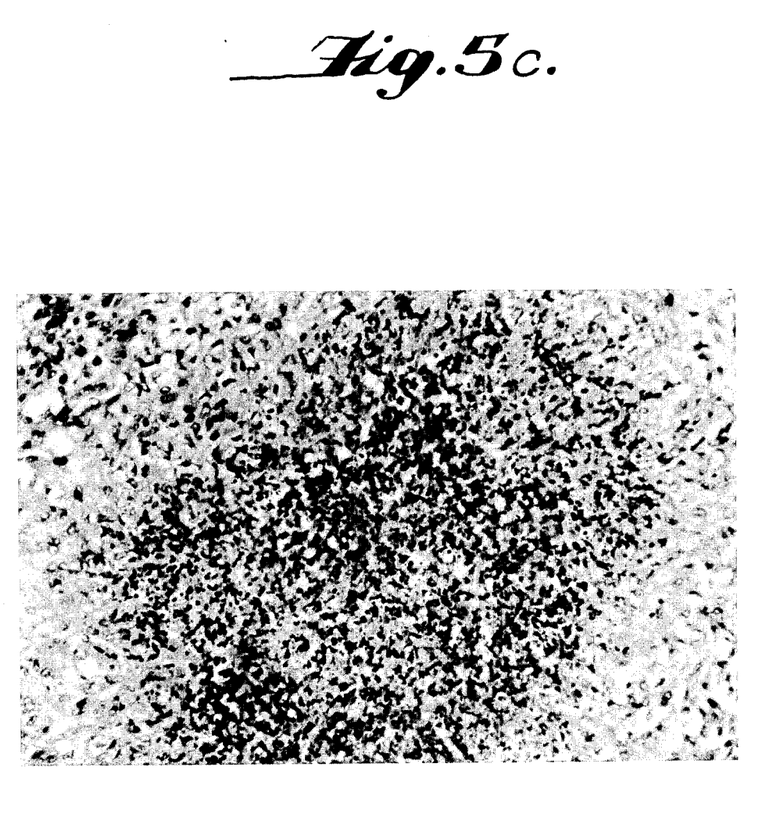

Histological features of PG-APS induced granulomatous hepatitis and the modifying effect of BABIM At autopsy, the Lewis rats with PG-APS injection (without BABIM) had a multitude of granulomata throughout the liver. The lesions most commonly arose within or in contact with a portal area, and on becoming larger, they bulged into the hepatic lobules and compressed the parenchymal cells. Only a few granulomata originated in the vicinity of the central veins. Initially, the granulomata were composed solely of histiocytes (FIG. 5A). Most of the cells had round open nuclei and ill-defined eosinophilic cytoplasm. Very occasional nuclei had a typical epithelioid cell configuration. Along the periphery of the larger lesions there were a few lymphocytes. They became more plentiful and admixed with plasma cells in the contact zone with the portal areas. Fibroblasts and rare multinucleated foreign body type giant cells were also noted in the outer layers of the granulomata. From a certain size onward, the granulomata had conspicuous central infiltrates of polymorphonuclear neutrophils and concomitantly underwent necrosis (FIGS. 5B and C). If large numbers of granulomata were present in a given section, they would often abut on one another, but they did not proceed to fuse completely.

In the BABIM-treated animals, the hepatic granulomata had the same size and makeup as that found in the untreated animals. However, even from a cursory glance at the histological sections, it was obvious that granulomata were much less common in the former group than in the latter. Actual counts of granulomata in identical 0.5 $cm^2$ sections of liver tissue confirmed that impression and revealed that BABIM treatment had brought about a two-thirds reduction in the number of lesions (Table 2). The difference in involvement between the two groups of animals was also expressed in significantly higher liver weights in the untreated rats than in the treated rats. The percentage of centrally necrotic lesions was about the same in the two groups, (approximately 50%). The total amounts of PG-APS fragments deposited in the livers of animals in both groups were nearly the same (Table 2).

Histological features of granulomatous splenitis and the effect of BABIM treatment Granulomatous inflammation in the spleen was encountered in all untreated rats and in three out of seven inhibitor-treated animals. In contrast to the round shape of the liver granulomata, splenic involvement was often in a geographic pattern.

TABLE 2

Weight, granulomatous disease, and type A streptococcal peptidoglycan polysaccharide (PG-APS) deposition in the liver of vehicle-treated and bis(5-amidino-2-benzimidazolyl) methane (BABIM)-treated rats*

| | Vehicle-treated rats (n = 8) | BABIM-treated rats (n = 7) |
|---|---|---|
| Weight of Liver (gm) | 18.5 ± 3.8 | 11.0 ± 3.5** |
| Granulomata | | |
| No. per section | 81.8 ± 34.5 | 25.6 ± 26.3*** |
| % with necrosis | 56 | 43 |

TABLE 2-continued

Weight, granulomatous disease, and type A streptococcal peptidoglycan polysaccharide (PG-APS) deposition in the liver of vehicle-treated and bis(5-amidino-2-benzimidazolyl) methane (BABIM)-treated rats*

|  | Vehicle-treated rats (n = 8) | BABIM-treated rats (n = 7) |
|---|---|---|
| PG-APS deposits (mg) | 0.226 ± 0.072 | 0.237 ± 0.055 |

*Values are the mean ± SD (except for the percentage of granulomata with necrosis). Mean ± SD body weight of the vehicle-treated rats was 164 ± 13.5 gm, and it was 177 ± 8.5 gm in the rats treated with BABIM.
**$P < 0.002$ versus vehicle-treated rats.
***$P < 0.005$ versus vehicle-treated rats.

There were extensive irregular areas of necrosis and neutrophilic infiltration, surrounded by histiocytes and proliferating fibroblasts. The lesions appeared to have originated in the red pulp, but often destroyed white pulp as well. In the non-granulomatous portions of the red pulp, there were accumulations of large numbers of myeloid cells of all stages of maturation, and there were also many megakaryocytes. Erythroid precursors were infrequent, however.

Table 3 lists the splenic disease scores for the two experimental groups. In the untreated group all animals were affected, having disease scores that ranged from 1 to 4, whereas in the BABIM recipients four out of the seven animals had no disease at all but three were rated the highest grade possible, (a score of 4). Statistically, there was no significant difference between the two groups.

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

TABLE 3

Extent of splenic granulomatous involvement in vehicle-treated and bis(5-amidino-2-benzimidazolyl) methane (BABIM)-treated rats*

| Vehicle-treated rats | | BABIM-treated rats | |
|---|---|---|---|
| Animal | Disease score | Animal | Disease score |
| 1 | 1 | 1 | 4 |
| 2 | 2 | 2 | 4 |
| 3 | 1 | 3 | 0 |
| 4 | 2 | 4 | 0 |
| 5 | 3 | 5 | 0 |
| 6 | 4 | 6 | 4 |
| 7 | 4 | 7 | 0 |
| 8 | 4 | | |
| Mean ± SD | 2.63 ± 1.3 | | 1.71 ± 1.5 |

*Disease was scored on a scale of 0–4, based on the percentage of granulomatous replacement of splenic parenchyma, where 0 = none, 1 = <25%, 2 = >25% but <50%, 3 = >50% but <75%, and 4 = >75%. The mean ± SD score in BABIM-treated rats was not statistically significantly different from that in the vehicle-treated group ($P > 0.2$).

What is claimed is:

1. A method of treating arthritis which comprises administering to a patient having arthritis, an arthritis treating effective amount of bis-(5-amidino-2-benzimidazolyl)methane and a pharmaceutically acceptable carrier.

2. The method of claim 1 wherein said administration is parenteral.

3. A method of treating bone marrow hyperplasia which comprises administering to a patient having bone marrow hyperplasia, a hyperplasia treating effective amount of bis-(5-amidino-2-benzimidazolyl)methane, and a pharmaceutically acceptable carrier.

4. A method of treating osteitis which comprises administering to a patient having osteitis an osteitis treating effective amount of bis-(5-amidino-2-benzimidazolyl)methane, and a pharmaceutically acceptable carrier.

5. A method of treating synovitis which comprises administering to a patient having synovitis, a synovitis treating effective amount of bis-(5-amidino-2-benzimidazolyl)methane, and a pharmaceutically acceptable carrier.

6. A method of treating granulomatosis which comprises administering to a patient having granulomatosis, a granulomatosis effective amount of bis-(5-amidino-2-benzimidazolyl)methane, and a pharmaceutically acceptable carrier.

7. The method of claim 6 wherein said granulomatosis occurs in the liver.

8. The method of claim 6 wherein said granulomatosis occurs in the spleen.

* * * * *